(12) United States Patent
Friesen et al.

(10) Patent No.: US 12,272,966 B2
(45) Date of Patent: *Apr. 8, 2025

(54) METHOD AND SYSTEM FOR WIRELESS CHARGING OF IMPLANTABLE MEDICAL DEVICES

(71) Applicant: CraniUS LLC, Baltimore, MD (US)

(72) Inventors: Owen Friesen, Baltimore, MD (US); Eleni Daskopoulou, Baltimore, MD (US); Farooq Akhtar, Baltimore, MD (US); Vikarie Elliott, Baltimore, MD (US); Conner Delahanty, Baltimore, MD (US); John Cai, Baltimore, MD (US)

(73) Assignee: CraniUS LLC, Baltimore, MD (US)

( * ) Notice: Subject to any disclaimer, the term of this patent is extended or adjusted under 35 U.S.C. 154(b) by 124 days.

This patent is subject to a terminal disclaimer.

(21) Appl. No.: 18/333,601

(22) Filed: Jun. 13, 2023

(65) Prior Publication Data

US 2023/0327493 A1 Oct. 12, 2023

Related U.S. Application Data

(63) Continuation of application No. 17/957,088, filed on Sep. 30, 2022, now Pat. No. 11,770,028.

(Continued)

(51) Int. Cl.
*H02J 7/00* (2006.01)
*A61L 31/08* (2006.01)
(Continued)

(52) U.S. Cl.
CPC ............ *H02J 50/27* (2016.02); *A61L 31/088* (2013.01); *A61L 31/14* (2013.01); *H01Q 1/085* (2013.01);
(Continued)

(58) Field of Classification Search
CPC .......... H02J 50/20; H02J 50/27; H02J 50/402; H02J 50/70; A61L 31/088; A61L 31/14; H01Q 1/085; H01Q 9/0485
(Continued)

(56) References Cited

U.S. PATENT DOCUMENTS

2002/0064676 A1 5/2002 Bokisa et al.
2008/0216846 A1* 9/2008 Levin ..................... A61B 17/22
128/898

(Continued)

OTHER PUBLICATIONS

MRIsafety.com, "RF Bion Microstimulator", Safety Topic/Article #254, 2023, pp. 1-8 https://www.mrisafety.com/SafetyInformation_view.php?editid1=254.
(Continued)

*Primary Examiner* — Zixuan Zhou
(74) *Attorney, Agent, or Firm* — Maier & Maier, PLLC (57) ABSTRACT

An RF charging system for implantable medical devices. The RF charging system includes a radio frequency (RF) signal, a first antenna configured to transmit the RF signal, a second antenna configured to receive the RF signal transmitted by the first antenna, tune characteristics of the RF signal, and improve power transfer with impedance matching circuitry, an RF to direct current (DC) converter configured to convert the RF signal of the second antenna into a DC signal, and a battery management circuit configured to receive the DC signal and provide voltage to a battery.

19 Claims, 6 Drawing Sheets

Related U.S. Application Data (60) Provisional application No. 63/251,143, filed on Oct. 1, 2021.

(51) Int. Cl.

| | | |
|---|---|---|
| *A61L 31/14* | (2006.01) | |
| *H01Q 1/08* | (2006.01) | |
| *H01Q 9/04* | (2006.01) | |
| *H02J 50/20* | (2016.01) | |
| *H02J 50/27* | (2016.01) | |
| *H02J 50/40* | (2016.01) | |
| *H02J 50/70* | (2016.01) | |

(52) U.S. Cl.
CPC .......... *H01Q 9/0485* (2013.01); *H02J 50/20* (2016.02); *H02J 50/402* (2020.01); *H02J 50/70* (2016.02)

(58) Field of Classification Search
USPC .......................................... 320/108; 307/104
See application file for complete search history.

(56) References Cited

U.S. PATENT DOCUMENTS

| | | |
|---|---|---|
| 2010/0181964 A1 | 7/2010 | Huggins et al. |
| 2013/0035034 A1 | 2/2013 | Kim et al. |
| 2015/0066112 A1* | 3/2015 | Parramon ............ A61N 1/3605 607/59 |
| 2016/0111208 A1 | 4/2016 | Park et al. |
| 2018/0055406 A1* | 3/2018 | Mandal .................. A61B 5/369 |
| 2020/0306533 A1 | 10/2020 | Deshazo et al. |
| 2023/0079910 A1 | 3/2023 | Laughery et al. |

OTHER PUBLICATIONS

Kim et al., "Soft Subdermal implant capable of wireless battery charging and programmable controls for applications in optogenetics", Published online: Jan. 22, 2021, Nature Communication, p. 13 (Year: 2021).

International Search Report and Written Opinion issue don Jan. 9, 2023, in corresponding International Application No. PCT/US2022/045330, 10 pages.

Alex Burton et al., "Wireless, battery-free, and fully implantable electrical neurostimulation in freely moving rodents", Microsystems & Nanoengineering (2021)7: 62, https://doi.org/10.1038/s41378-021-00294-7, 12 pgs.

Choong Yeon Kim et al., "Soft subdermal implant capable of wireless battery charging and programmable controls for applications in optogenetics", Nature Communications, vol. 12, Article No. 535 (2021), 13 pgs.

Julian Moore et al., "Applications of Wireless Power Transfer in Medicine: State-of-the-Art Reviews", Annals of Biomedical Engineering, vol. 47, No. 1, Jan. 2019, pp. 22-38, 18 pgs.

Mustafa F. Mahmood et al., "Hybrid Coils-Based Wireless Power Transfer for Intelligent Sensors", Sensors 2020, 20, 2549, Published: Apr. 30, 2020, 25 pgs.

\* cited by examiner

METHOD AND SYSTEM FOR WIRELESS CHARGING OF IMPLANTABLE MEDICAL DEVICES

CROSS-REFERENCE TO RELATED APPLICATIONS

This application is a continuation of U.S. patent application Ser. No. 17/957,088, filed Sep. 30, 2022, and entitled "Method and System for Wireless Charging of Implantable Medical Devices", which claims priority to U.S. Provisional Application No. 63/251,143, filed Oct. 1, 2021, and entitled "Method and System for Wireless Charging of Implantable Medical Devices", the entire contents of which are hereby incorporated by reference.

The embodiments generally relate to the field of chronic medicine delivery, refillable needle reservoirs, wearable technology, Bluetooth-enabled devices, wireless charging power platforms, state-of-the-art biotechnology, craniofacial implants, neurosurgery, neuroplastic surgery, implantable neurotechnology, plastic surgery, craniomaxillofacial surgery, orthopedic surgery, and neuro-oncology, and specifically to the field of improving form and function of permanent implants for anatomical replacement of both hard and soft tissue components.

BACKGROUND

The present invention relates generally to the field of implantable medical devices, and more particularly, to a wireless charging system for implantable medical devices and a wireless charging method thereof, a method of preparing a wireless charging system for implantable medical devices, and more particularly, for allowing implantable medical devices to remain safe, effective, and compatible in light of all common medical imaging necessities including magnetic resonance imaging (MRI), computed topography scanning (CT), and X-ray.

In the medical device industry, a magnetic resonance imaging (MRI) compatible radio frequency (RF) wireless power transfer technology can be used to charge surgical power tools, handheld diagnostic instruments, and portable infusion pumps—all of which remain outside the human body. By using an MRI compatible wireless RF charging system, such extra-anatomical medical devices can be more easily charged without requiring multiple charging cradles and cords.

There is an increasing need to develop an MRI compatible RF wireless charging system with more efficient power transmission and smaller MRI artifacts for implantable medical devices that can be permanently placed within the human body and allows for any type of necessary imaging for disease evaluation.

RF wireless charging systems commonly use surface finishes incorporating ferromagnetic nickel. Electroless Nickel Immersion Gold (ENIG) is the most common of these. This process of forming an ENIG surface finish includes depositing a thicker nickel layer of 2.5 to 5 microns on top of a copper substrate, then covering the nickel layer with a gold layer of 50 to 230 nanometers. When the substrate is reflowed, the gold layer wicks into the solder and the solder bonds to the nickel, instead of directly to the copper.

Further, many existing implantable medical devices recharge via an inductive coil, which interacts with the electromagnetic fields generated by the MRI as a result of its shape and material properties. Inductive coils can also have a magnetic backing plate, which would further interfere with the MRI. This approach prevents the device in which it is being used from being MRI lucent, as induction coils cause significant radiology artifact, which may hinder treatment of a patient. For example, for patients with chronic brain disease, including malignant brain tumors, the efficacy of MRI imaging for tumor surveillance could be hindered by the effects of the inductive coil obstructing a partial area of the brain from being seen.

At the same time, there is a need for a method of preparing an MRI compatible RF wireless charging system with improved MRI lucency, MRI safety, and/or MRI compatibility, with lucency being defined as absent imaging interference, thereby allowing internal neighboring anatomy (i.e. an organ) of interest to be precisely evaluated without imaging distortion (i.e. an MRI lucent medical device implanted in the skull and soft tissue space that allows uninterrupted brain imaging), safety referring to the implanted medical device being present inside the patient's body during an actively engaged MRI room without any potential danger, and compatibility being defined as persistent function of the device even after patient undergoes active MRI scanning (i.e. no alteration of the medical device's function pre-MRI to post-MRI).

SUMMARY

An exemplary embodiment may relate to an MRI safe, MRI compatible, and/or MRI lucent RF wireless charging system for both short-term and long-term implantable medical devices and an MRI safe, MRI compatible, and/or MRI lucent RF wireless charging method thereof, and a method of preparing an MRI safe, MRI compatible, and/or MRI lucent RF wireless charging system for implantable medical devices.

In an exemplary embodiment, there may be an RF wireless charging system, which may use an oscillator or external signal generator to produce an RF signal. The RF signal may be a high frequency signal, for example, a signal on the order of 1 GHz. The RF signal may be sent to an antenna or antenna array, and then transmitted into free space. The RF energy may be picked up at distance by a receiver antenna.

In an exemplary embodiment, there may be a radio frequency to direct current (RF-DC) converter integrated with a voltage regulation circuit on a charging system, allowing for effective RF power transfer at different frequency bands. Furthermore, there may be an implanted printed circuit board (PCB) with a surface finish that prevents corrosion and enables soldering of connections and components. The surface finish could be, for example, an immersion silver (IAg) finish, or could alternatively be another finish, such as an electroless nickel immersion gold (ENIG) finish, or some other finish known in the art.

In an exemplary embodiment, the charging system may include an implanted PCB. The PCB may undergo a surface finish process. The surface finish process may include depositing a silver layer onto an exposed substrate, such as a copper substrate, before electronic components are soldered on to protect the copper from oxidation. A reflow treatment may be performed, which causes the silver layer to wick into the solder and the solder to bond directly to the copper substrate. This may configure an alternative MRI lucent wireless power transmission system beyond RF, which in turn, may remove risk for negative artifact appearance and/or harmful imaging obstruction necessary for human body evaluation from, for example, an MRI machine.

It may be noted that the alternate RF-DC converter integrated with a voltage regulation circuit, and alternative MRI lucent wireless power transmission system beyond RF, may eliminate the use of ferromagnetic nickel in the PCB design, improving MRI performance. While small amounts of nickel in, for example, capacitors, may be necessary and acceptable, the more that the amount of ferromagnetic material present can be reduced, the smaller the resultant artifact will be. Therefore, an improved MRI compatible RF wireless charging system may be provided, which provides a dual benefit of both patient safety and enhanced imaging effectiveness.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments", or "invention" do not require that all embodiments of the invention include the discussed feature, advantage or mode of operation.

Exemplary embodiments described herein may relate to an MRI compatible RF wireless charging system for implantable medical devices, which may include a radio frequency to direct current (RF-DC) converter integrated with a voltage regulation circuit on the charging system to allow for more effective transfer of RF power, may include an implanted printed circuit board (PCB) coated with an immersion silver (IAg) finish, and/or may include an alternative MRI lucent wireless power transmission system beyond RF. The RF power may be of different frequency bands, including but not limited to, 902 to 928 MHz, 2.4 to 2.4835 GHz, and 5.725 to 5.825 GHz ISM bands.

Exemplary embodiments described herein may also relate to a method of preparing an MRI compatible RF wireless charging system for implantable medical devices, which may include a charging system with an RF-DC converter integrated with a voltage regulation circuit, and/or performing a surface finish process on implanted PCBs.

In an exemplary embodiment, there may be an RF wireless charging system, which may use an oscillator or external signal generator to produce an RF signal. The RF signal may be a high frequency signal, for example, a signal on the order of 1 GHz. The RF signal may be sent to an antenna or antenna array, and then transmitted into free space. The RF signal may be picked up at distance by a receiver antenna. The receiver antenna may be tuned so that it does not resonate at certain frequencies, for example, to avoid frequencies found in an MRI machine, which may make the RF wireless charging system more MRI lucent and/or allow for room-scale wireless charging.

In an exemplary embodiment, the surface finish process of the implanted PCB may include depositing 5 to 18 microinches (127 to 457 nanometers) of silver layer onto an exposed substrate, such as a copper substrate, before electronic components are soldered on. This may protect the copper from oxidation. Then, a reflow treatment may be performed, and the silver layer may wick into the solder and the solder may bond directly to the copper substrate, which may configure the alternative MRI lucent wireless power transmission system beyond RF.

In alternative embodiments, other forms of surface finish may be used, for example, electroless nickel immersion gold (ENIG), which may involve the deposition of a layer of nickel covered by a thin layer of gold over the exposed copper, hot air solder level (HASL), or lead-free HASL. Alternatively, any other surface finish method known in the art may be used, as desired. Other finishes can include, but are not limited to, organic solderability preservative (OSP), immersion tin (ISn), electroless nickel electroless palladium immersion gold (ENEPIG), electrolytic wire bondable gold, and electrolytic hard gold.

In some embodiments, alternative MRI safe, MRI compatible, and/or MRI lucent wireless power transfer beyond RF may be included within the power transfer system. For example, the alternative MRI lucent wireless power transfer options may include, but are not limited to, one or more of inductive power transfer; capacitive power transfer; ultrasound power transfer; infrared power transfer; RF power transfer; power transfer via direct electrical contact; and/or kinetic power capture.

In other embodiments, different antennas may be utilized, including ceramic chip antennas and PCB antennas. The transmitter may also take different forms and may transmit more power. One transmitter may be utilized, or a plurality of transmitters may be used in concert, in order to increase power transmission. In other embodiments, individual components in the system, such as capacitors, resistors, and crystals, may be swapped out with comparable versions with smaller MRI artifacts. The layer count on the PCB may change, and one or several field programmable gate arrays (FPGAs) or application specific integrated circuits (ASICs) may be used. Furthermore, antennas may be housed within several types of structures for close-by proximity and effective wireless charging, including, but not limited to, baseball cap/headwear, a headphone-type system, and/or pillow case-like apparatus.

Variations of the implantable device having different power and processing needs may also be developed. For example, additional sensors may be included within the implantable device, including but not limited to flow rate sensors; battery voltage sensors; charging power sensors; regulator error sensors; temperature sensors; pressure sensors; shock sensors; and/or ultrasound sensors. Relatedly, flow-sensing capability on catheters, imaging devices (i.e.

implantable ultrasound devices), and/or medicine delivery pumps may be tied into the existing processor.

Other embodiments may involve a different processor and associated circuitry, for example, applications of the wireless power and control system for future implanted ultrasound devices and other applications with higher processing and power demands.

In an exemplary embodiment, the RF-DC converter integrated with a voltage regulation circuit may allow for continuous power transfer, and/or may include impedance matching circuitry to tune the RF characteristics of the receiver antenna and increase power transfer. The impedance matching circuitry may be, for example, a PI-match impedance matching circuit, or an L-match circuit. In other embodiments, various other types of impedance matching circuitry may be used, including, but not limited to an L-match circuit, a T-network, a split capacitor network, a transmatch circuit, matching stubs, and dedicated matching devices.

In an exemplary embodiment, the RF-DC conversion circuit may be an individual module connected to the system. In a different embodiment, the RF-DC circuit may be integrated into the PCB, which may remove extraneous circuity and/or allow for greater control over RF characteristics.

In an exemplary embodiment, there may be an RF supply tracking system. The RF supply tracking system may steer the location of maximum power transmission to be aimed directly at the receiver of the implantable medical device. The RF supply tracking system may include, but is not limited to, computer vision, IR sensing, use of an integrated IMU, and/or Bluetooth direction finding.

In an exemplary embodiment, the MRI compatible RF wireless charging system may be embedded in an implantable medical device, including, but not limited to, high-profile subcutaneous skull, skull and soft tissue, or brain implants, low-profile skull, skull and soft tissue, or head implants, knee replacements, hip replacements, and/or shoulder replacements.

In other embodiments, the MRI compatible RF wireless charging system may be used in a medical or non-medical device for medical or non-medical purposes.

Figure 1:
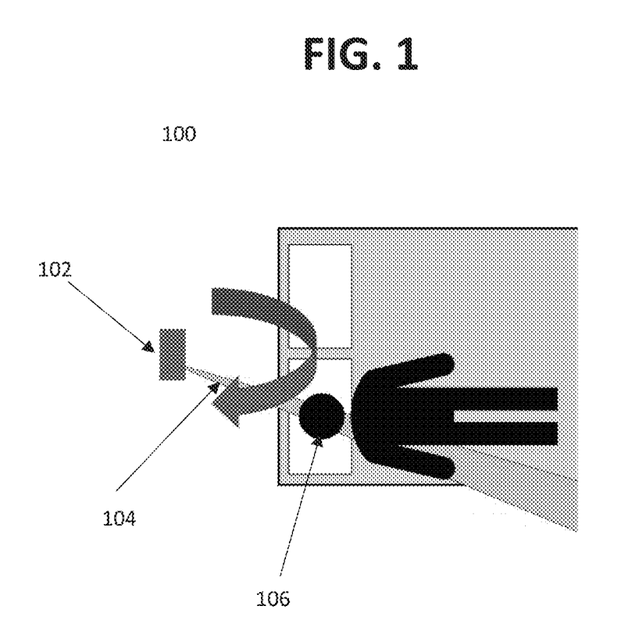
FIG. 1 illustrates power tracking working in concert with a directed antenna to provide power transfer.

FIG. 1 is an illustration of an RF supply tracking system 100. The RF tracking system 100 may include a base station 102, which may include, for example, a power transmitter and/or a tracking system. The base station 102 may transmit RF power 104. The RF power 104 may be directed to a device, such as a medical device implanted in a person's head 106.

Figure 2:
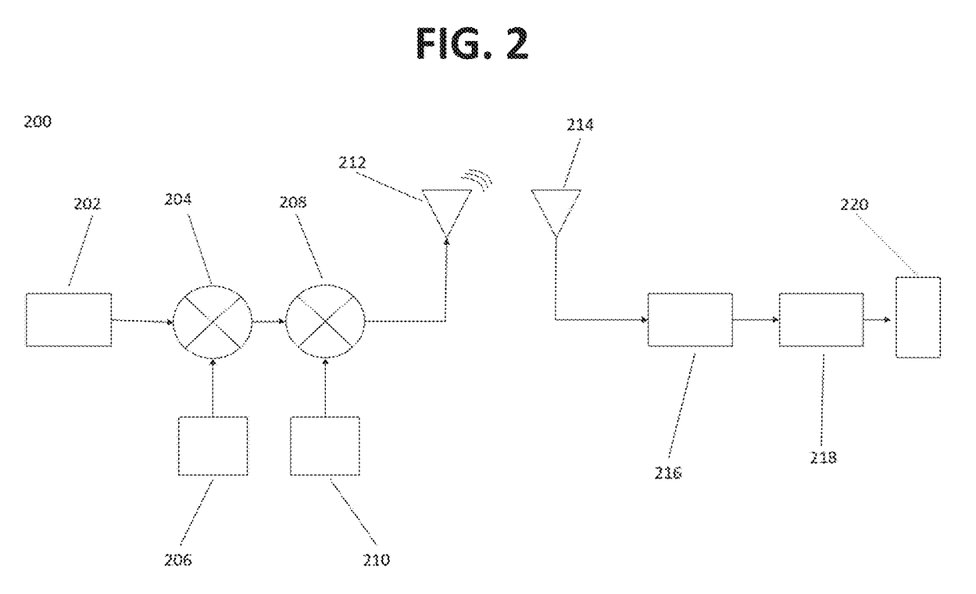
FIG. 2 illustrates the base station signal processing process.

FIG. 2 is an illustration of a base station signal processing process 200. The signal processing process 200 may begin with a raw signal 202. The raw signal 202 may go through a primary modulation step 204. The primary modulation step 204 may be, for example, continuous phase modulation using the raw signal 202 and a carrier signal 206. The signal processing process 200 may then include a secondary modulation step 208. The secondary modulation step 208 may be, for example, a direct sequence spread spectrum modulation, using the output from the primary modulation step 204 and a pseudorandom noise sequence 210. The signal outputted from the secondary modulation step 208 may then be transmitted by a transmitter 212 and then received by a receiver 214. The signal may then go through an RF to DC converter 216. After being converted to DC, the power may go through a battery management circuit (BMC) 218 and may finally arrive at the battery 220 of, for example, a medical implant.

Figure 3:
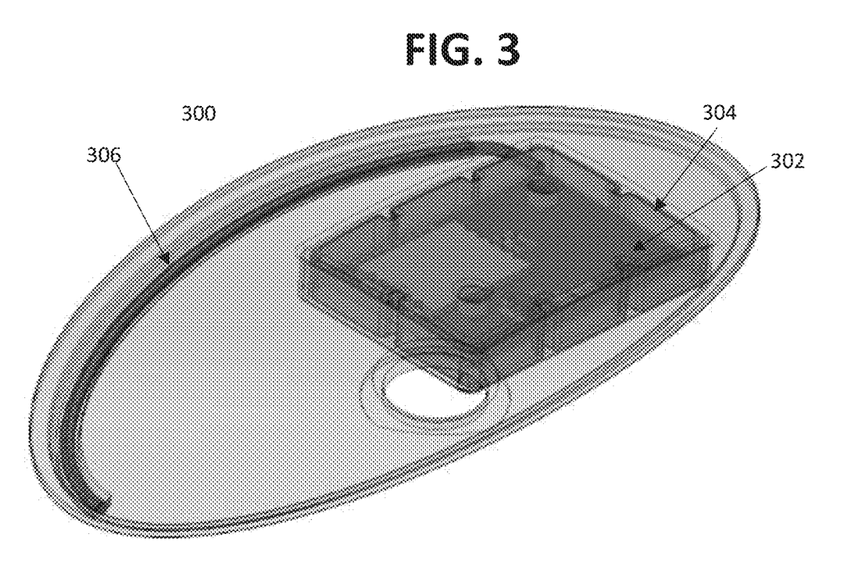
FIG. 3 is a CAD model of an exemplary device lid.

FIG. 3 is a CAD drawing of an exemplary device lid 300. The device lid 300 may include a PCB 302. The PCB 302 may be embedded in a coating or potting material 304, for example, but not limited to, parylene, epoxy, silicone, urethane, polyacrylate, and/or dielectric gels. The device lid 300 may further include a housing for an antenna 306. The housing for the antenna 306 may define the shape of the antenna, and may be built to allow for various types of antennas, such as, but not limited to, a ceramic chip antenna, a whip antenna, a PCB antenna, or any other antenna commonly used in the art.

Figure 4:
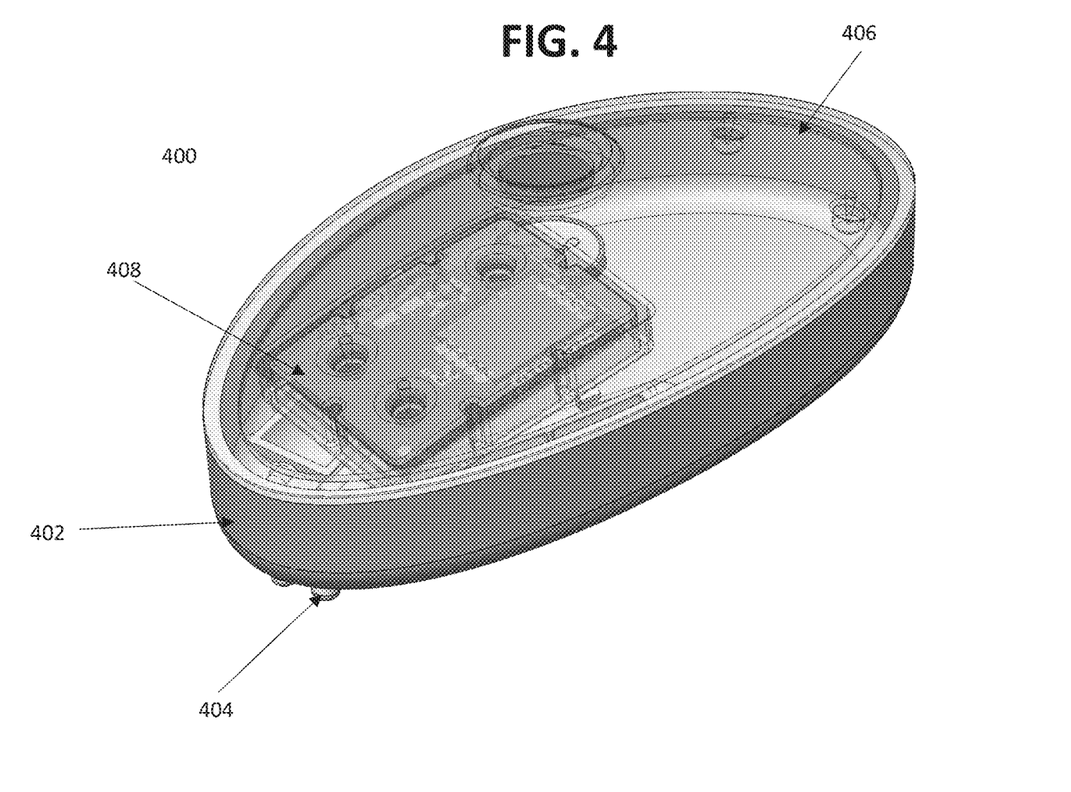
FIG. 4 is a CAD model of an exemplary device body and lid.

FIG. 4 is a CAD model of an exemplary device 400 body and lid. The exemplary device 400 may have a device body 402. The device body 402 may contain one or more components, such as a reservoir, sensors, etc. The device body may also have one or more external outlets 404 such as, for example, catheters or nozzles. The device 400 may further include a device lid 406. A chip 408 may be positioned in the device lid 406. The positioning of the chip 408 in the device lid 406 may isolate MRI artifact so that it impinges only on the device 400 and not on underlying tissue, such as the brain or a tumor, located beneath the device 400.

Figure 5:
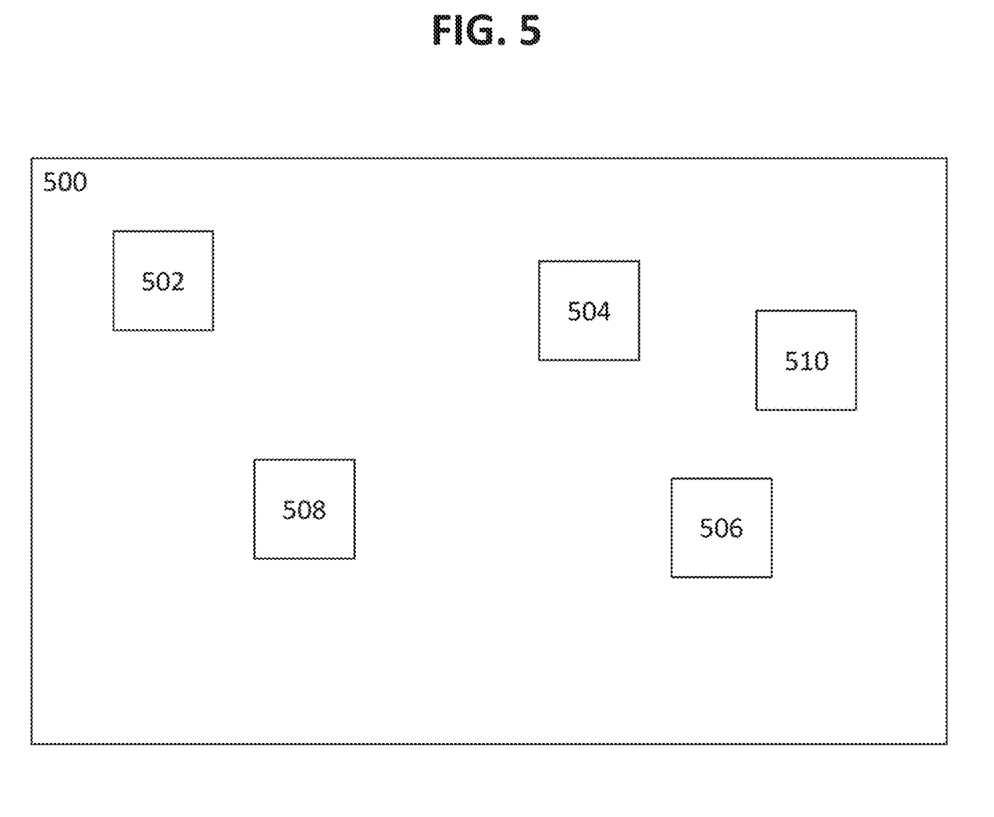
FIG. 5 is an exemplary block chip diagram with some exemplary components.

FIG. 5 is an exemplary block chip diagram with some exemplary components. The block chip diagram may include a chip 500. The chip 500 may be composed of bulk dielectric material, for example FR4 TG180, and may further be composed of layers of a conductive material such as copper. The chip 500 may have a surface finish such as IAg or ENIG. On the chip 500 there may be one or more components, which may include a Bluetooth antenna 502. The one or more components may also include a processor 504, and one or more sensors 506, such as, but not limited to, a pressure sensor and/or temperature sensor. The chip 500 may additionally have antenna matching circuity 508 and may have a RF-DC converter 510.

Figure 6:
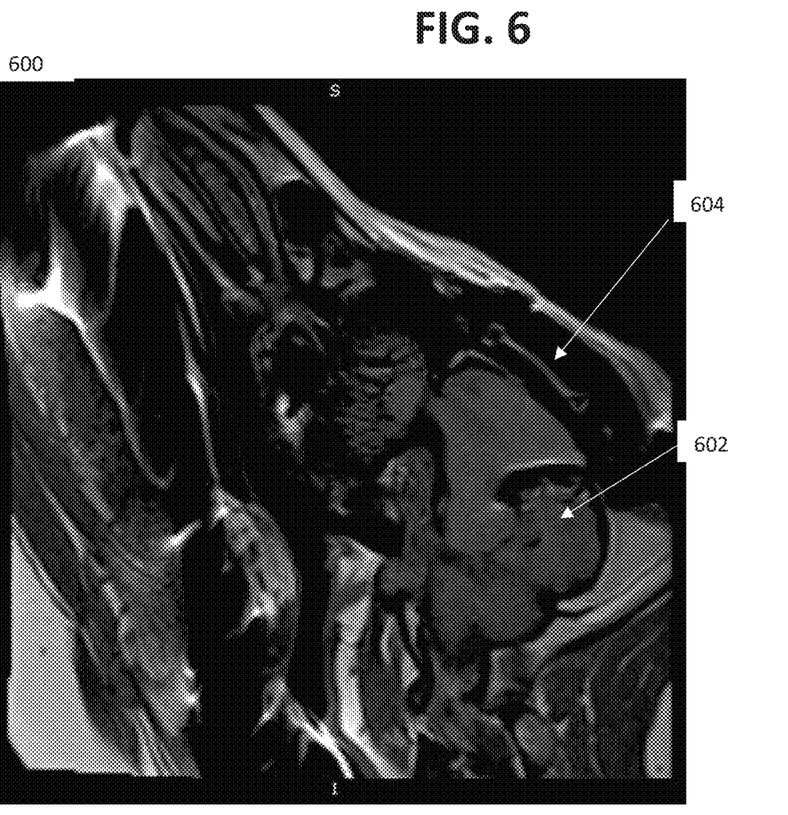
FIG. 6. is an MRI picture of a pig with an exemplary device embedded.

FIG. 6. is an MRI picture 600 of a pig with an exemplary device embedded. The MRI 600 picture shows the brain 602 of a test subject, the exemplary device 604 may be MRI lucent, that is, the exemplary device 604 may not interfere with the imaging of the subject's brain 602.

As a result, it may be appreciated that a more efficient MRI compatible RF wireless power transfer system for implantable devices with higher processing capacity, more power transmission, and improved MRI lucency and MRI compatibility may be achieved.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A magnetic resonance imaging (MRI) lucent, wirelessly-chargeable, implantable medical device, comprising:
   an MRI-lucent housing; and
   an MRI-lucent antenna contained in the housing and configured to wirelessly receive an electromagnetic signal from a signal source external to the housing, wherein the signal source further comprises:

a primary modulator configured to combine a raw signal with a carrier signal to provide a signal having continuous phase modulation; and a secondary modulator configured to combine the signal having continuous phase modulation with a pseudorandom noise sequence to provide a signal having direct sequence spread spectrum modulation, wherein the signal having direct sequence spread spectrum modulation is input to an antenna of the signal source.

2. The implantable medical device of claim 1, wherein the electromagnetic signal is a radio frequency (RF) signal.

3. The implantable medical device of claim 1, further comprising a direct current (DC) converter contained in the housing and configured to convert the electromagnetic signal to direct current.

4. The implantable medical device of claim 2, further comprising a direct current (DC) converter contained in the housing and configured to convert the RF signal to direct current.

5. The implantable medical device of claim 3, further comprising a battery contained in the housing and chargeable by the direct current.

6. The implantable medical device of claim 4, further comprising a battery contained in the housing and chargeable by the direct current.

7. The implantable medical device of claim 1, wherein the device is implanted in an organism and the signal source is external to the organism.

8. The implantable medical device of claim 1, further comprising one or more of a reservoir, a sensor, an external outlet, and a catheter.

9. A wireless charging system for implantable medical devices, comprising:
a wirelessly-chargeable, implantable medical device having an MRI-lucent housing and an MRI-lucent antenna contained in the housing; and
a signal source external to the housing;
wherein the antenna is configured to wirelessly receive an electromagnetic signal from the signal source; and the signal source further comprises:
a primary modulator configured to combine a raw signal with a carrier signal to provide a signal having continuous phase modulation; and
a secondary modulator configured to combine the signal having continuous phase modulation with a pseudorandom noise sequence to provide a signal having direct sequence spread spectrum modulation, wherein the signal having direct sequence spread spectrum modulation is input to an antenna of the signal source.

10. The wireless charging system of claim 9, wherein the electromagnetic signal is a radio frequency (RF) signal.

11. The wireless charging system of claim 9, further comprising a direct current (DC) converter contained in the housing and configured to convert the electromagnetic signal to direct current.

12. The wireless charging system of claim 10, further comprising a direct current (DC) converter contained in the housing and configured to convert the RF signal to direct current.

13. The wireless charging system of claim 11, further comprising a battery contained in the housing and chargeable by the direct current.

14. The wireless charging system of claim 12, further comprising a battery contained in the housing and chargeable by the direct current.

15. The wireless charging system of claim 9, wherein the device is implanted in an organism and the signal source is external to the organism.

16. The wireless charging system of claim 10, the signal source further comprising a tracking system configured to direct the RF signal emitted by the signal source towards the antenna of the implantable medical device.

17. A method for wireless charging, comprising:
wirelessly transmitting an RF signal from a signal source; and
receiving the RF signal with a magnetic resonance imaging (MRI) lucent antenna that is contained in an MRI-lucent medical device housing;
wherein the signal source is external to the housing, and further comprises a primary modulator configured to combine a raw signal with a carrier signal to provide a signal having continuous phase modulation; and
a secondary modulator configured to combine the signal having continuous phase modulation with a pseudorandom noise sequence to provide a signal having direct sequence spread spectrum modulation, wherein the signal having direct sequence spread spectrum modulation is input to an antenna of the signal source.

18. The method of claim 17, further comprising directing the RF signal emitted by the signal source towards the antenna.

19. The method of claim 17, wherein the housing is implanted in an organism and the signal source is external to the organism.

* * * * *